United States Patent [19]
Komatsu et al.

[11] Patent Number: 5,438,393
[45] Date of Patent: Aug. 1, 1995

[54] POWDER FLUIDITY DETECTING APPARATUS WHICH INCLUDES A PIEZOELECTRIC ELEMENT

[75] Inventors: Katsuaki Komatsu; Kazunori Yamamoto; Shinichi Nishi, all of Hino, Japan

[73] Assignee: Konica Corporation, Tokyo, Japan

[21] Appl. No.: 154,749

[22] Filed: Nov. 18, 1993

[30] Foreign Application Priority Data

Nov. 26, 1992 [JP] Japan .................. 4-317128
Nov. 27, 1992 [JP] Japan .................. 4-318882
Nov. 27, 1992 [JP] Japan .................. 4-319060
Nov. 27, 1992 [JP] Japan .................. 4-319061

[51] Int. Cl.⁶ .................................. G03G 21/00
[52] U.S. Cl. .................. 355/246; 118/689; 355/208
[58] Field of Search ............... 355/203, 208, 245, 246, 355/260; 118/653, 689, 690, 694; 73/580, DIG. 4

[56] References Cited

U.S. PATENT DOCUMENTS

| | | | |
|---|---|---|---|
| 4,314,242 | 2/1982 | Kuru et al. | 340/617 |
| 4,397,265 | 8/1983 | Terashima | 118/694 |
| 5,006,897 | 4/1991 | Rimai et al. | 355/246 |
| 5,235,388 | 8/1993 | Rimai et al. | 355/246 |
| 5,237,371 | 8/1993 | Hori | 355/246 |
| 5,285,243 | 2/1994 | Rimai et al. | 355/246 |

FOREIGN PATENT DOCUMENTS

| | | |
|---|---|---|
| 2936280 | 3/1980 | Germany . |
| 57-38482 | 3/1982 | Japan . |
| 62-157070 | 7/1987 | Japan . |
| 2-141758 | 5/1990 | Japan .................. 355/260 |

OTHER PUBLICATIONS

Patent Abstracts of Japan, vol. 004, No. 168 (P-037), Nov. 20, 1980 & JP-A-55 114 981 (TDK Corp.), Sep. 4, 1980.
Patent Abstracts of Japan, vol. 007, No. 231 (P-229), Oct. 13, 1983 & JP-A-58 121 072 (Ricoh KK), Jul. 19, 1983.
Patent Abstracts of Japan, vol. 015, No. 176 (P-1198), May 7, 1991 & JP-A-03 037 592 (TDK Corp.), Feb. 18, 1991.
Patent Abstracts of Japan, vol. 010, No. 364 (P-524), Dec. 5, 1986 & JP-A-61 158 353 (Casio Computer Co., Ltd; Others 01), Jul. 18,1986.
Patent Abstracts of Japan, vol. 009, No. 120 (P-358), May 24, 1985 & JP-A-60 004 820 (Nouken Kogy KK), Jan. 11, 1985.
European Search Report.

*Primary Examiner*—William J. Royer
*Attorney, Agent, or Firm*—Frishauf, Holtz, Goodman & Woodward

[57] ABSTRACT

A method for detecting a fluidity of powder includes the steps of: (a) making the powder come into contact with a surface of a piezoelectric element which is parallel with an oscillating direction of the piezoelectric element that generates traverse wave oscillations; (b) detecting electrical characteristics of the piezoelectric element under a condition of resonance; and (c) detecting the fluidity of the powder in accordance with a change in the electrical characteristics with respect to a reference value.

29 Claims, 15 Drawing Sheets

SHEAR WAVE VIBRATION
(TRANSVERSE WAVE)

LONGITUDINAL VIBRATION
(LONGITUDINAL WAVE)

POWDER FLUIDITY DETECTING APPARATUS WHICH INCLUDES A PIEZOELECTRIC ELEMENT

BACKGROUND OF THE INVENTION

The present invention relates to a method and an apparatus for detecting the fluidity of powder.

In a copier or a printer, powdery toner is supplied to a latent image formed on a photoreceptor so that the latent image can be developed. Therefore, the powdery toner loaded in a developing unit is conveyed to the photoreceptor. In the case of toner to be mixed with a magnetic carrier, toner and carrier are stirred in the developing unit.

In this case, when the toner or the mixture (developer) of toner and carrier has a low fluidity, a sufficient amount of toner can not be supplied to the photoreceptor, or the toner can not be sufficiently mixed with carrier, so that the performance of development and transfer is lowered and the image quality is deteriorated, that is, unevenness of image density is caused. In order to solve the above problems, it is preferable to increase the fluidity of the developer or to improve the development and transfer function.

However, a detector to detect the fluidity of developer has not been provided yet. Therefore, the above problems can not be solved until now.

In general, when an angle of repose of powder is measured, the fluidity can be known. However, such a method takes a long period of time, and moreover it is impossible to apply the method to the measurement of powder put in a container.

In this connection, there is conventionally provided a detector to detect a residual amount of toner by oscillating longitudinal ultrasonic waves, however, this type of detector only detects the existence of residual toner, so that the fluidity of powder can not be detected with ultrasonic waves.

In view of the aforesaid conventional problems, the present invention has been achieved. The first object of the present invention is to provide a fluidity detection method and apparatus by which the fluidity of powder can be directly measured while the powder is put in a container.

Conventionally, an image forming apparatus has been known, in which: an electrostatic latent image is formed on a photoreceptor drum by an optical exposure system; the electrostatic latent image is developed with a developing unit using toner; the toner image is transferred onto a recording sheet; and the transferred toner image is fixed. This image forming apparatus is disclosed in Japanese Patent Application Open to Public Inspection Nos. 38482/1982 and 157070/1987.

Both one component and two component type developers are used for the above developing unit. The two component type developer is composed of magnetic carrier particles and nonmagnetic synthetic resin toner particles, wherein the magnetic carrier particles and nonmagnetic synthetic resin toner particles are mixed at an appropriate mixing ratio. Therefore, the toner particles mixed with the carrier particles are conveyed to a development sleeve of the developing unit, and deposited on an electrostatic latent image portion on the photoreceptor surface so that a toner image can be formed.

In the case where the two component type developer is used, only toner is consumed, and carrier is repeatedly circulated in the developing unit. Therefore, a toner concentration sensor to measure the concentration of toner is provided in the developing unit, and toner is appropriately replenished in accordance with the result of the detection, and the developer is stirred in the developing unit so that the developer can be appropriately charged and mixed at a predetermined mixing ratio.

In this connection, in the toner image formation described above, when the fluidity of developer (toner or a mixture of toner and carrier) is lowered, the adhesive force among the developer particles is increased. Accordingly, even when the substantial toner concentration is appropriate, the developed toner image becomes uneven and blurred, so that the image quality is deteriorated.

However, the conventional image forming apparatus are not provided with a sensor to detect the fluidity of developer. Therefore, the occurrence of defective images caused by the lowered fluidity can not be avoided.

In order to detect the fluidity of powder such as developer, there is provided a method by which an angle of repose of powder is measured. However, this method takes a long period of time, and moreover it is difficult to measure an angle of repose while the powder is put in a container. Therefore, it is substantially impossible to apply this method to an image forming apparatus so as to solve the problem of lowered fluidity.

In view of the aforesaid problems, the present invention has been achieved. The second object of the present invention is to provide an apparatus to which a sensor to quickly detect the fluidity of developer is provided so that the deterioration of image quality can be avoided in accordance with the result of detection of fluidity.

As a method to detect an amount of residual toner in a hopper, there is provided a method in which a microswitch is turned on and off in accordance with the weight of toner, and also there is provided a method in which an amount of residual toner is detected with an electrical means by measuring a dielectric constant of toner.

However, toner is essentially light, and the dielectric constant of toner is not large. Accordingly, the aforesaid residual toner amount detection methods can not provide sufficient sensitivity, stability and reliability.

In order to solve the above problems, the present inventors have proposed a method to detect an amount of residual toner characterized in that: an oscillating member is provided in a toner hopper or on a hopper wall surface; and an amount of toner deposited on the oscillating member is detected by an amount of displacement of the oscillating member, for example, the resonance frequency of the oscillating member. This method is disclosed in Japanese Patent Application Open to Public Inspection No. 36874/1980.

Specifically, the aforesaid oscillating member is a piezoelectric element oscillated in a thickness direction, that is, a piezoelectric element generating longitudinal waves, and the piezoelectric element is arranged so that the toner can be deposited on a surface of the piezoelectric element perpendicular to the oscillating direction. Therefore, an amount of residual toner can be detected when a difference is found between the oscillation characteristics.

However, by the aforesaid residual toner detection method, a toner amount is detected when a pressure of toner (weight of toner) impressed upon the piezoelectric element in an oscillating direction is measured. Accordingly, the following problems are caused: The detection characteristics are changed according to the type of toner and the condition of toner coagulation, so that the piezoelectric element must be selected each time the toner type is changed. Also, when the toner is coagulated due to moisture, it is impossible to ensure the stability of detection.

The present invention has been achieved while consideration is also given to the above problems. The third object of the present invention is to provide a residual toner amount detection apparatus by which the high detection stability can be ensured irrespective of the type of toner and the condition of toner coagulation.

Consideration is given to the problems described before, and in the present invention, powder is made to come into contact with a surface parallel with the oscillating direction of an oscillating element, and when a change in the electric characteristics of the oscillating element is measured, the condition of powder can be detected. In this case, the condition of powder is defined as the fluidity and residual amount.

SUMMARY OF THE INVENTION

In order to accomplish the first object, the present invention is to provide a method to detect the fluidity of powder, comprising the steps of: making the powder come into contact with a surface parallel with the oscillating direction of a piezoelectric element that generates transverse wave oscillation; detecting the electrical characteristics of the piezoelectric element under a condition of resonance; and detecting the fluidity of the powder in accordance with a change in the electrical characteristics with respect to a reference value. By the method described above, the fluidity of powder, which is one of the conditions of powder, can be detected.

For example, the change in the electrical characteristics can be detected when a change in impedance, that in resonance frequency or that in resonance sharpness Q is detected.

The powder fluidity detection apparatus according to the present invention is constructed in the following manner: A piezoelectric element generating a transverse wave oscillation is arranged so that powder is contacted with a surface parallel with an oscillating direction of the piezoelectric element. Electrical characteristics of the piezoelectric element are detected under a resonance condition. A detection means is provided which detects the fluidity of the powder in accordance with a change in the electrical characteristics of the piezoelectric element with respect to a reference value.

In this case, the aforesaid detection means detects a change in the electrical characteristics in the form of change in impedance, resonance frequency or resonance sharpness Q.

Under a resonance condition, the electrical characteristics of a piezoelectric element generating a transverse wave oscillation are varied in accordance with the fluidity of powder. Therefore, when a change in the electrical characteristics is detected with respect to a reference value (for example, a value in the case of contact with powder), the fluidity of the powder can be detected.

For example, the electrical characteristics are changed under a resonance condition in the following manner: When the fluidity of powder is lowered, the viscous resistance is increased. Accordingly, the impedance is also increased in accordance with the increase in the resistance R. Therefore, when a change in the impedance is detected, the fluidity of powder can be found.

As the impedance is increased in accordance with the increase of the viscous resistance of powder, the resonance frequency is lowered. Therefore, when a change in the resonance frequency is detected, the fluidity of powder can be found.

In the same manner, as the resistance R is increased in accordance with the increase of the viscous resistance of powder, the resonance sharpness Q is lowered in the case of resonance. Accordingly, when a change in the resonance sharpness Q is detected, the fluidity of powder can be also found.

In order to accomplish the second object of the present invention, the present invention is to provide a fluidity sensor in an image forming apparatus in which an electrostatic latent image formed on a photoreceptor is developed with toner, wherein the fluidity sensor detects the fluidity of developer used for the development in the following manner: the developer used for toner development is contacted with a surface of a shear ultrasonic wave oscillating element emitting transverse ultrasonic waves, wherein the surface is parallel with an oscillating direction of the shear ultrasonic wave oscillating element; and the fluidity of the developer is detected in accordance with a change in the oscillation characteristics of the shear ultrasonic wave oscillating element.

In this case, it is preferable to provide a fluidity judgment means to judge the deterioration of developer in accordance with a detection signal sent from the fluidity sensor, and it is also possible to provide a display means to display a judgment result in the case where the deterioration of fluidity has been judged by the fluidity judgment means.

It is also preferable to provide a charging potential control means to control a charging potential of the photoreceptor in accordance with the detection signal sent from the fluidity sensor.

It is also preferable to provide a toner concentration control means to control the toner concentration in the development unit in accordance with the detection signal sent from the fluidity sensor.

Further, a drying means to dry the developer may be provided, and a drying control means may be also provided which selectively activates the drying means in accordance with the detection signal sent from the fluidity sensor.

In the case where the aforesaid developer is a two-component developer composed of toner and carrier, and a stirring means is provided so as to stir the toner and carrier, a stirring control means may be provided, which controls a drive force of the stirring means in accordance with the detection signal sent from the fluidity sensor.

Also, an oscillating body to oscillate the developer to solve the coagulation of the developer may be provided, and an oscillation control means may be provided which controls the oscillation in accordance with the detection signal sent from the fluidity sensor.

The aforesaid fluidity sensor may be provided in at least one of the toner cartridge, toner hopper, toner conveyance path and developing unit.

In the image forming apparatus described above, a fluidity sensor is provided, which is characterized in that: developer is made to come into contact with a surface parallel with an oscillating direction of a transverse ultrasonic wave oscillating element emitting shear ultrasonic waves; and the fluidity sensor detects a change in the oscillation characteristics of the shear ultrasonic wave oscillating element when a load of the oscillating element is changed due to a change in the fluidity of developer. In this way, the fluidity of developer can be simply detected by the fluidity sensor even when the developer is put in a container.

When the fluidity of developer is lowered, the image quality is deteriorated. Therefore, when the deterioration of fluidity is detected by the fluidity sensor for which the shear ultrasonic wave oscillating element is used, the detection result is displayed. In this way, it is warned that the fluidity of developer is lowered and there is a possibility of deterioration in image quality.

In the case where the fluidity of developer is lowered, it becomes difficult to uniformly deposit the toner on the photoreceptor surface, which causes uneven development. Therefore, in accordance with the result of detection conducted by the fluidity sensor, a charging potential of the photoreceptor is controlled so that the deterioration of deposition of toner can be compensated.

In order to prevent the occurrence of blur of a toner image caused by the deteriorated fluidity of developer, the toner concentration is increased when the deteriorated fluidity is detected by a sensor.

Since the fluidity of developer is presumably deteriorated by moisture, a drier means for drying the developer is provided, and the developer is dried by the drier means so as to recover the fluidity of the developer in the case where the deteriorated fluidity has been detected.

In the case where a two-component developer composed of toner and carrier is used, a stirring means to mix the toner and carrier is generally provided. In this case, when the deteriorated fluidity has been detected by a fluidity sensor, the driving force of the stirring means is increased so as to recover the fluidity of developer by the action of the stirring means.

Alternatively, an oscillating member to oscillate the developer is differently provided for solving the problem of coagulation of the developer, and the developer is oscillated by the oscillating member to recover the fluidity of developer when the deteriorated fluidity has been detected by the fluidity sensor.

The aforesaid fluidity sensor may be provided in one of the toner cartridge, toner hopper, toner conveyance passage developing unit and the like. Therefore, the fluidity of developer can be detected while the developer is put in a commonly used container of the image forming apparatus.

In order to accomplish the third object of the present invention, in an image forming apparatus including a developing unit to develop with toner an electrostatic latent image on a photoreceptor, a piezoelectric element to generate shear waves is attached to a toner container from which toner is supplied to the developing unit, so that the toner can be deposited on a surface which is parallel to a direction of the oscillation generated by the piezoelectric element. When a change in the impedance of the piezoelectric element is measured in this way, a residual amount of toner in the container can be detected. By the apparatus described above, the residual amount of toner, which is one of the conditions of toner, can be detected.

In the piezoelectric element which generates shear waves, the impedance is changed by the viscosity of a medium coming into contact with a surface which is parallel with an oscillation direction of the piezoelectric element. Accordingly, when the image forming apparatus is constructed in such a manner that a contact surface of the piezoelectric element comes into contact with toner, the impedance is greatly changed between when the surface is contacted with toner, and when an amount of residual toner is lowered and the surface is contacted with air. Therefore, the residual amount of toner can be stably detected.

BRIEF DESCRIPTION OF THE DRAWINGS

In the detailed description of the preferred embodiments of the invention presented blow, reference is made to the accompanying drawings in which.

DETAILED DESCRIPTION OF THE INVENTION

With reference to the accompanying drawings, an embodiment to accomplish the first object will be described as follows.

Figure 1:
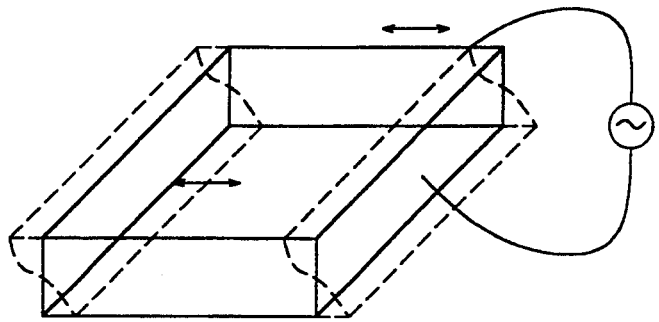
FIG. 1(A) is a perspective view of a piezoelectric element used for the present invention generating shear waves, in which an oscillating direction is illustrated.
FIG. 1(B) is a perspective view of a piezoelectric element generating longitudinal waves, in which an oscillating direction is illustrated.
Figure 1:
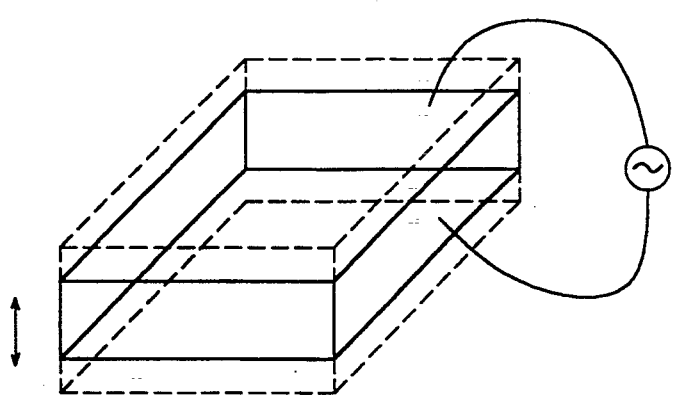

FIGS. 1(A) and 1(B) are views showing the oscillating direction of a piezoelectric element. In accordance with a direction in which an electric field is impressed and also in accordance with a direction of the crystals of the piezoelectric element, the direction of oscillation can be selectively determined. In the case of a conventional residual toner amount detection sensor, the pressure of toner in a hopper is detected, so that the oscillating direction is perpendicular to a boundary surface between the toner and the piezoelectric element as illustrated in FIG. 1(B) . That is, in the conventional residual toner amount detection sensor, longitudinal waves and longitudinal oscillation are generated.

On the other hand, the piezoelectric element used for an embodiment of the present invention is provided for detecting the fluidity of toner, and the oscillating direction is parallel with a toner contacting surface, that is, a boundary surface as illustrated in FIG. 1(A). That is, the piezoelectric element generates transverse waves, in other words, the piezoelectric element generates shear waves.

Figure 2:
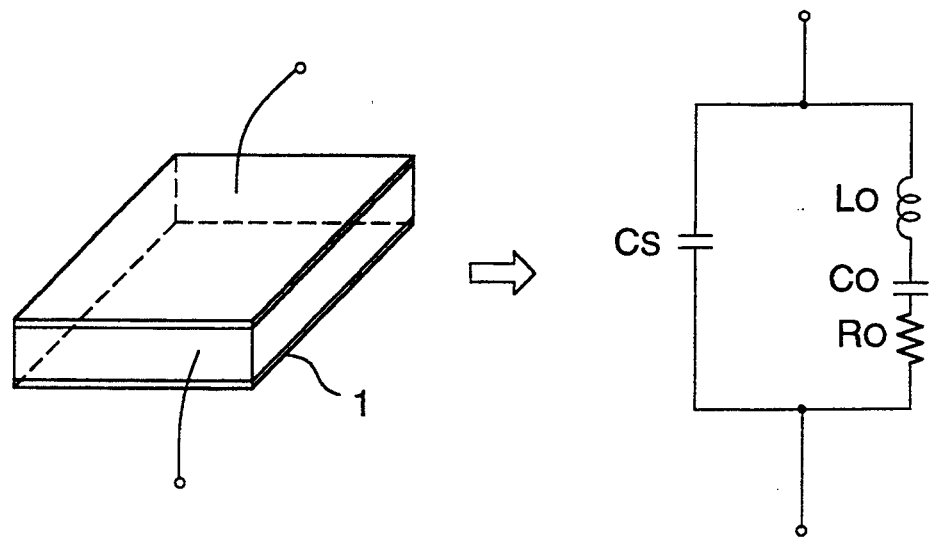
FIG. 2 is a circuit diagram showing an equivalent circuit of the piezoelectric element used for the present invention.

FIG. 2 is a view showing an equivalent circuit of electrical impedance of the piezoelectric element generating shear waves. The piezoelectric element 1 generates a mechanical oscillation of natural frequency determined by the thickness and material of the piezoelectric element 1. The electrical impedance of the piezoelectric element 1 is approximated as shown in FIG. 2.

The aforesaid electrical impedance is affected by a medium coming into contact with the surface of the piezoelectric element. In the case where the surface is longitudinally oscillated, the impedance is changed in accordance with the pressure and density of the medium. This principle is applied to the aforesaid residual toner amount sensor and liquid level sensor.

On the other hand, in the case of the aforesaid piezoelectric element 1 in which the oscillating direction of transverse waves is parallel with the boundary surface, the impedance is changed in accordance with the viscosity of a medium coming into contact with the boundary surface. Conventionally, a change in impedance has not been investigated when the medium is powdery. However, the present applicant has discovered that the impedance of a piezoelectric element generating transverse waves is changed by the fluidity of powder coming into contact with a boundary surface which is parallel with the oscillating direction of the piezoelectric element. Due to the foregoing, they have invented a new method by which the fluidity of powder can be measured in accordance with a difference of electrical characteristics between when powder comes into contact with the boundary surface, and when powder does not come into contact with the boundary surface.

In order to measure a change in the electrical characteristics before and after the contact of powder, the following specific methods are provided.

(1) A change in the absolute value of impedance is measured.

(2) A change in the resonance frequency is measured.

(3) Resonance sharpness Q is measured.

Figure 3:
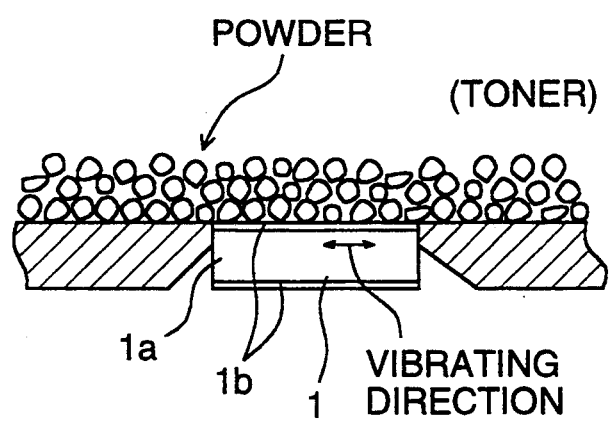
FIG. 3 is a sectional view showing a condition of a piezoelectric element used for an embodiment to which the first method to accomplish the first object is applied.
Figure 4:
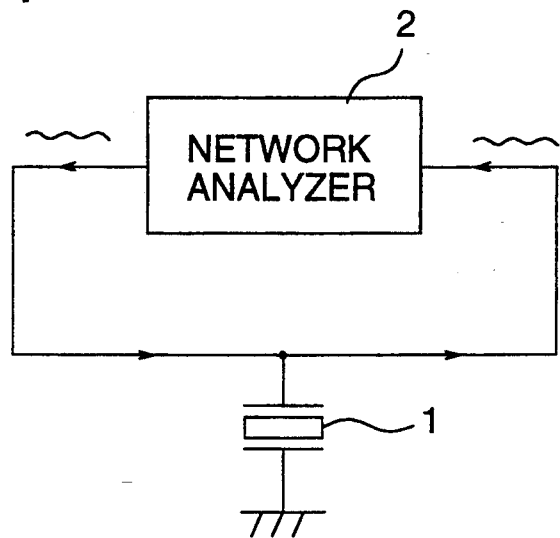
FIG. 4 is a circuit diagram of the aforesaid embodiment.

With reference to FIGS. 3 and 4, an example of the apparatus to which the aforesaid method (1) is applied will be explained as follows. In FIG. 3, the piezoelectric element 1 generating transverse waves is constructed in the following manner: chromium is vapor-deposited on the front and reverse surfaces of a crystal oscillator 1a so that electrodes 1b can be formed; and the piezoelectric element 1 is attached onto an outer wall of the toner hopper so that one of the electrodes 1b can be contacted with powder.

Figure 5:
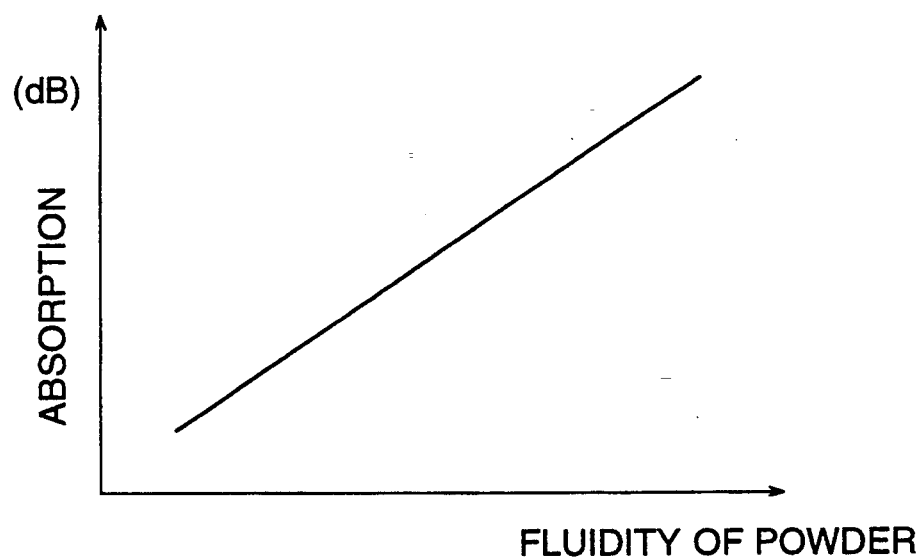
FIG. 5 is a diagram showing a relation between the fluidity of powder and the signal absorption level of a piezoelectric element in the aforesaid embodiment.

FIG. 4 shows a circuit of this apparatus. In FIG. 4, a network analyzer 2 functions as a device by which a ratio of the amplitude of an AC signal inputted into the piezoelectric element 1 to the amplitude that has passed through the piezoelectric element 1 is measured when the frequency is changed. A change in impedance caused by powder (medium) is expressed by a change in the ratio of an input ted amplitude to an outputted amplitude, that is, "an inputted amplitude to the network analyzer 2"/"an outputted amplitude from the network analyzer 2". FIG. 5 shows an exemplary relation between the fluidity of powder and the ratio of an inputted amplitude to an outputted amplitude.

Figure 6:
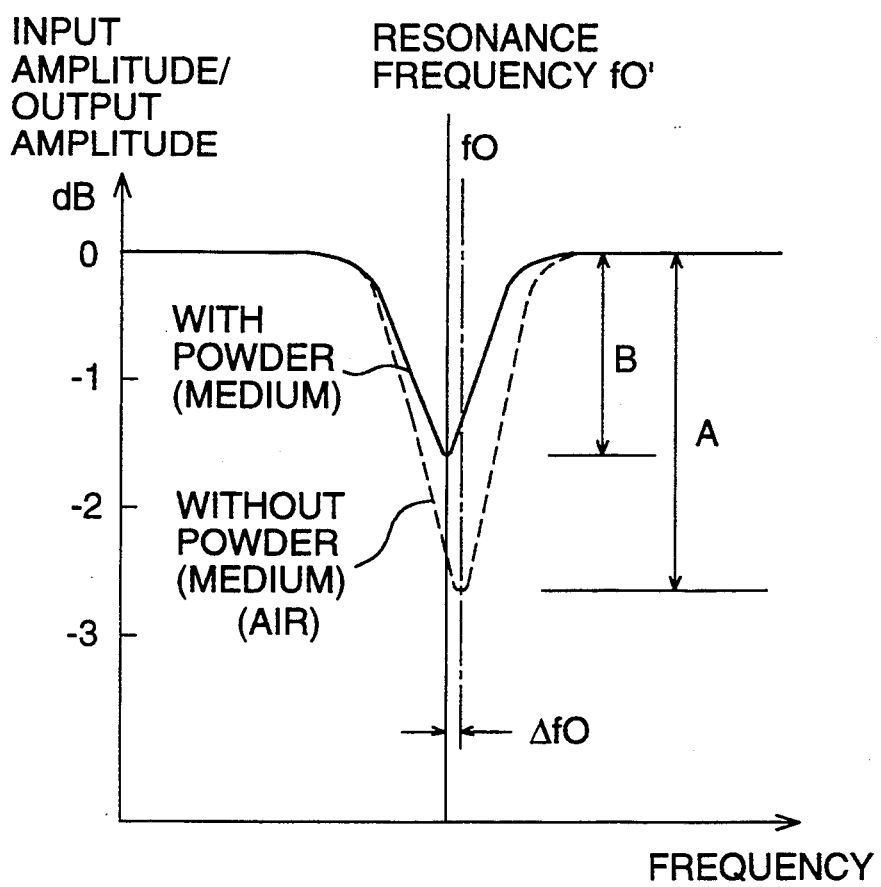
FIG. 6 is a diagram showing a relation between the oscillating frequency of a piezoelectric element and a ratio of an input and an output amplitude in the aforesaid embodiment.

The frequency of an AC signal outputted from the network analyzer 2 is scanned, and a point is measured where the piezoelectric element 1 resonates and absorbs the AC signal. The result of measurement is shown in FIG. 6. As illustrated in FIG. 6, the inputted and outputted amplitude ratio A is found at the absorption point (the resonance point) when the surface is not contacted with powder (medium), and the inputted and outputted amplitude ratio B is found at the absorption point (the resonance point) when the surface is contacted with powder. In this case, the viscous resistance of powder is much higher than that of air. Therefore, when the surface is contacted with powder, the impedance is very high and the absorption ratio is lowered, so that the inputted and outputted amplitude ratio B becomes much smaller than A (absolute value).

When the fluidity of powder is lowered, the viscous resistance is increased. Accordingly, the inputted and outputted amplitude ratio B is further lowered.

When a ratio (=B/A) of the inputted and outputted amplitude ratio A in the case where powder is not contacted, o the inputted and outputted amplitude ratio B in the case where powder is contacted, is quantitatively detected.

Figure 7:
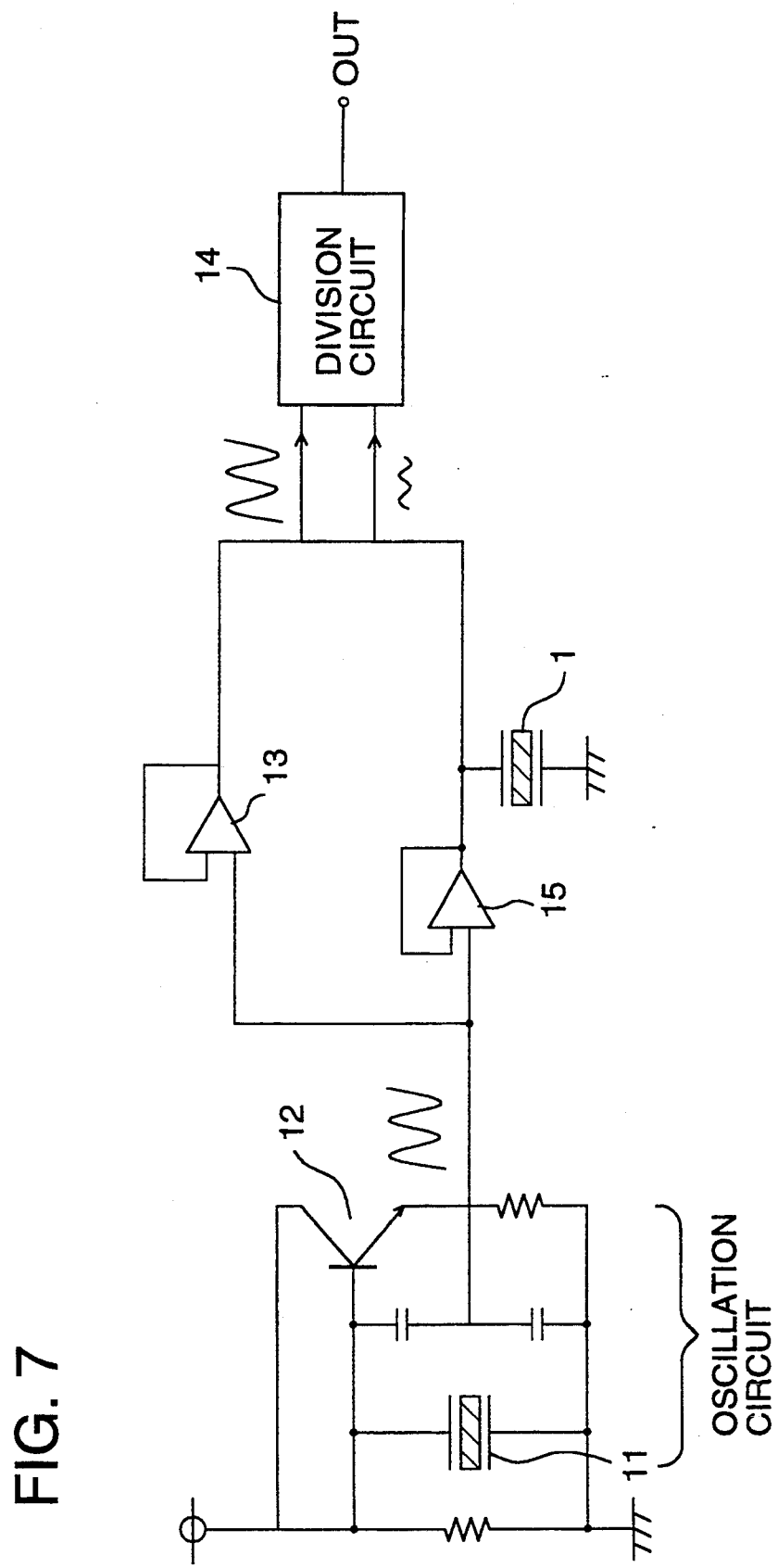
FIG. 7 is a circuit diagram of another embodiment to which the first method is applied.
Figure 8:
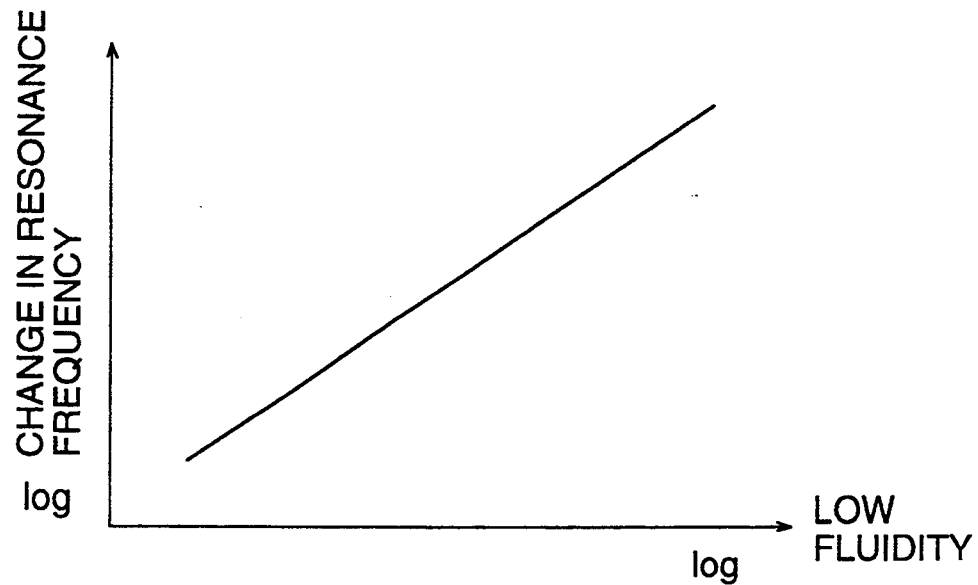
FIG. 8 is a diagram showing a relation between the fluidity of powder and the resonance frequency of a piezoelectric element.

In this example, the network analyzer 2 is employed, however, the piezoelectric element 1 may be made to resonate with the resonance frequency f, and the inputted and outputted amplitude ratio (=B/A) may be detected at that time. In this method, the measurement is conducted at one point of frequency, so that the measurement circuit can be simplified, however, it is difficult to appropriately select the central frequency. Strictly speaking, the resonance frequency in the case of contact of powder is a little different from that in the case of non-contact, which will be described later. However, in the case where the inputted and outputted amplitude ratio is found, the resonance frequency $f_0$ in the case of non-contact may be used for finding the inputted and outputted amplitude ratio in the case of contact because the error is small. FIG. 7 is a view showing a measurement circuit of this example. As shown in the drawing, an oscillating circuit includes an amplifying circuit composed of an oscillator 11 and a transistor 12. An AC signal oscillated by the oscillating circuit is inputted into a division circuit 14 through a buffer 13, and at the same time, the signal passes through a buffer 15, and then the signal is absorbed by the piezoelectric element 1 and inputted into the division circuit 14. In the division circuit 14, each signal is integrated, and then the integrated value is divided, so that a signal of the inputted and outputted amplitude ratio is outputted from the division circuit 14.

When this construction is employed, it is not necessary to make it resonate by scanning, and a resonance condition can be automatically provided. Therefore, the circuit structure can be simplified, and the manufacturing cost can be reduced. Consequently, it is easy to assemble it into a copier or a printer.

Since the two piezoelectric elements 1 and 11 have the same function and form, the same operation can be performed even when the outside factors such as temperature are varied. Therefore, the detection accuracy of the fluidity of powder is not affected by the outside factors, and further a difference between the individual oscillating elements can be compensated, so that a stable accuracy can be always maintained.

In the aforesaid circuit, when the oscillator 11 in the oscillating circuit and the piezoelectric element 1 functioning as a fluidity sensor are made of the same material and formed into the same configuration, the temperature can be compensated and also a difference between the individuals can be compensated.

Figure 9:
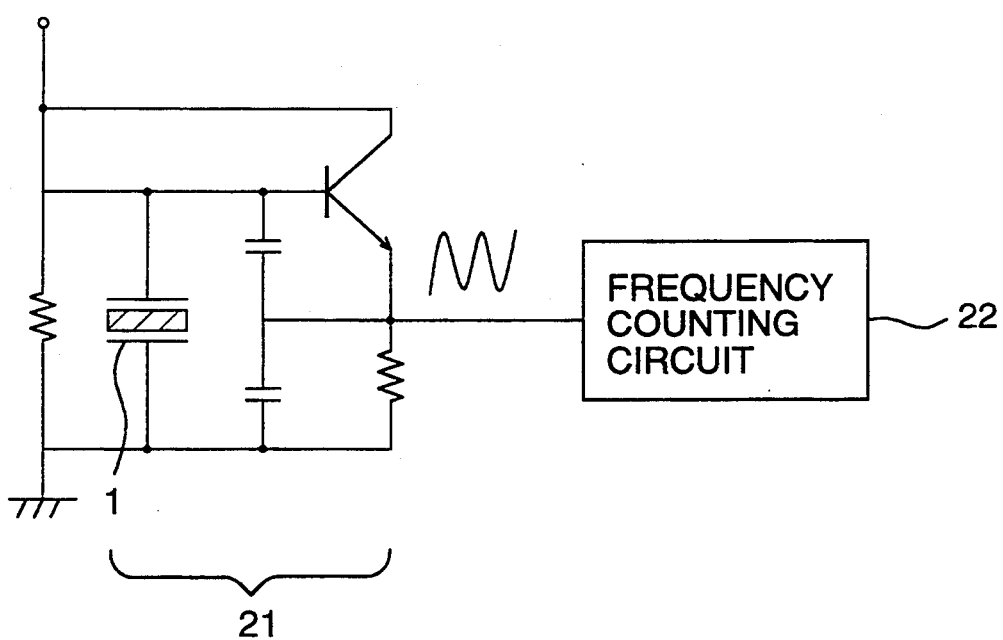
FIG. 9 is a circuit diagram of an embodiment to which the second method is applied to accomplish the first object of the present invention.

Next, with reference to FIG. 9, an example to which the method (2) is applied will be explained as follows.

As shown in FIG. 6, the resonance frequency $f_0'$ in the case where the piezoelectric element 1 is contacted with powder, is a little changed with respect to the resonance frequency $f_0$ in the case where the piezoelectric element 1 is non contacted with powder. This slippage between $f_0$ and $f_0'$ can be accurately measured with a high-class measuring instrument such as a network analyzer described above. However, when the measuring circuit shown in FIG. 9 is used, it can be easily measured.

In this measuring circuit, a self-excited oscillating circuit 21 is formed from the piezoelectric element 1 used as a powder fluidity sensor, and also a frequency counter circuit 22 to count the frequency of a signal oscillated by the self-excited oscillating circuit 21 is provided. The frequency $f_0$ of a signal oscillated by the self-excited oscillating circuit 21 before the surface comes into contact with powder, and the frequency $f_0'$ of a signal oscillated by the self-excited oscillating circuit 21 after the surface has come into contact with powder, are counted by the counter circuit 22, and the fluidity of powder is detected in accordance with a difference between both frequencies.

Figure 10:
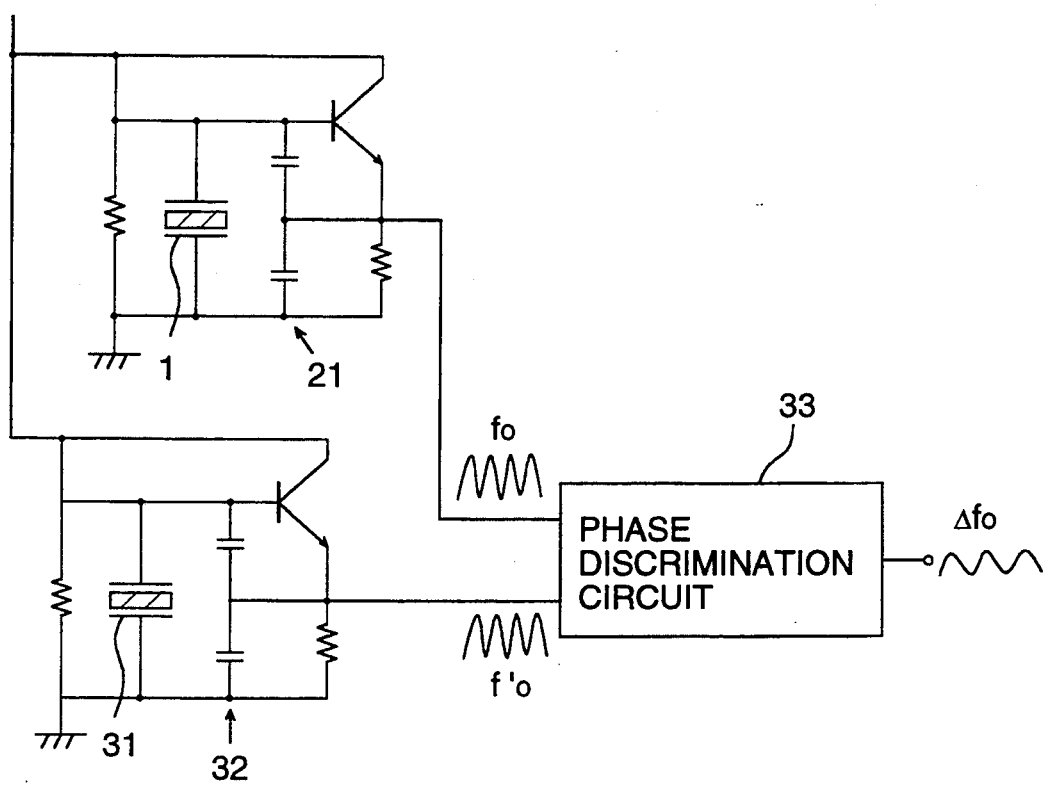
FIG. 10 is a circuit diagram of another embodiment to which the second method is applied.

FIG. 10 shows a circuit by which the detecting operation is further automatized. In this measuring circuit, a self-excited oscillating circuit 21 is formed from the piezoelectric element 1 used as a powder fluidity sensor, and an oscillator 31 made of the same material and configuration as those of the piezoelectric element 1 is connected to the self-excited oscillating circuit 32 in parallel. The signal outputs of the self-excited oscillating circuits 21, 32 are inputted into a phase discrimination circuit 33. The self-excited oscillating circuit oscillates at a resonance point in FIG. 6, wherein the resonance point is expressed by a trough in the drawing. When the oscillator 31 in the self-excited oscillating circuit 32 is not contacted with powder, the oscillating frequency of the oscillator 31 coincides with the oscillating frequency $f_0$ of the piezoelectric element 1 in the case the surface is not contacted with powder, and the piezoelectric element 1 oscillates with the frequency $f_0$ which is the same frequency in the case where the surface comes into contact with powder. These two oscillating frequency $f_0$ and $f_0'$ are inputted into the phase discriminating circuit 33, and a signal having a frequency corresponding to the difference $\Delta f_0 (=f_0 - f_0')$ between the oscillating frequencies $f_0$ and $f_0'$ is outputted from the phase discriminating circuit 33. Accordingly, when the frequency $\Delta f_0$ is measured, the fluidity of powder can be detected.

According to the circuit described above, in the same manner as the aforementioned example, it is not necessary to make it resonate by scanning, and a resonance condition can be automatically provided. Therefore, the circuit structure can be simplified, and the manufacturing cost can be reduced. Consequently, it is easy to assemble it into a copier or a printer.

Also, the piezoelectric oscillator 31 in the self-excited oscillating circuit 32, and the piezoelectric element 1 which functions as a fluidity sensor, have the same function and form. Therefore, the detection accuracy of the fluidity of powder is not affected by the outside factors such as temperature, and further a difference between the individual oscillating elements can be compensated in the same manner. In this example, the division circuit 14 (FIG. 7) corresponds to a level ratio detection circuit.

There are provided various types of self-excited oscillating circuits to which an oscillator is assembled. In this connection, the oscillating condition is determined by the resonance sharpness value Q. The resonance sharpness value Q is varied by a medium coming into contact with the boundary surface of an oscillator. The aforesaid method (3) utilizes this phenomenon. An embodiment of the method (3) will be explained as follows.

Figure 11:
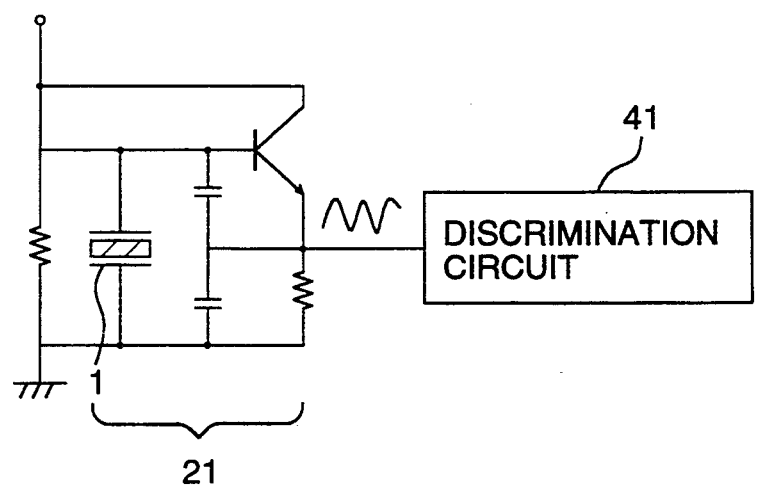
FIG. 11 is a circuit diagram of an embodiment to which the third method is applied to accomplish the first object of the present invention.

As shown in FIG. 11, an apparatus used for the method (3) includes a self-excited oscillating circuit 21 to which the piezoelectric element 1 is assembled, and a discrimination circuit 41 to discriminate a signal output sent from the self-excited oscillating circuit 21. When it is discriminated whether or not a signal is outputted from the self-excited oscillating circuit 21, it is judged whether or not the fluidity of powder is maintained to be not less than a reference level. That is, in FIG. 2 which is the equivalent circuit of the aforesaid oscillator, resonance sharpness Q is expressed by $Q = \omega_0 \cdot L_0 / R_0$. Therefore, when a load is given to the oscillator, $R_0$ is increased, so that the value of Q is decreased. Accordingly, the self-excited oscillation is stopped. Consequently, when the circuit conditions of the self-excited oscillating circuit 21 are appropriately selected, the self-excited oscillations are stopped at a point of time when the fluidity of powder is lowered to a certain value. In this way, when the self-excited oscillation is stopped, it can be detected that the fluidity of powder has been reduced to a value lower than the reference level. Alternatively, the fluidity of powder can be linearly measured in accordance with a resistance value of a variable resistor composing the oscillation circuit when the oscillation has been stopped.

As described above, according to the present invention, when the changes in various electric characteristics such as impedance, resonance frequency and resonance sharpness are detected, the fluidity of powder can be easily detected, and even under the condition that powder is put in a container, the fluidity can be highly accurately detected.

With reference to the accompanying drawings, an example to accomplish the second object will be described as follows.

Figure 12:
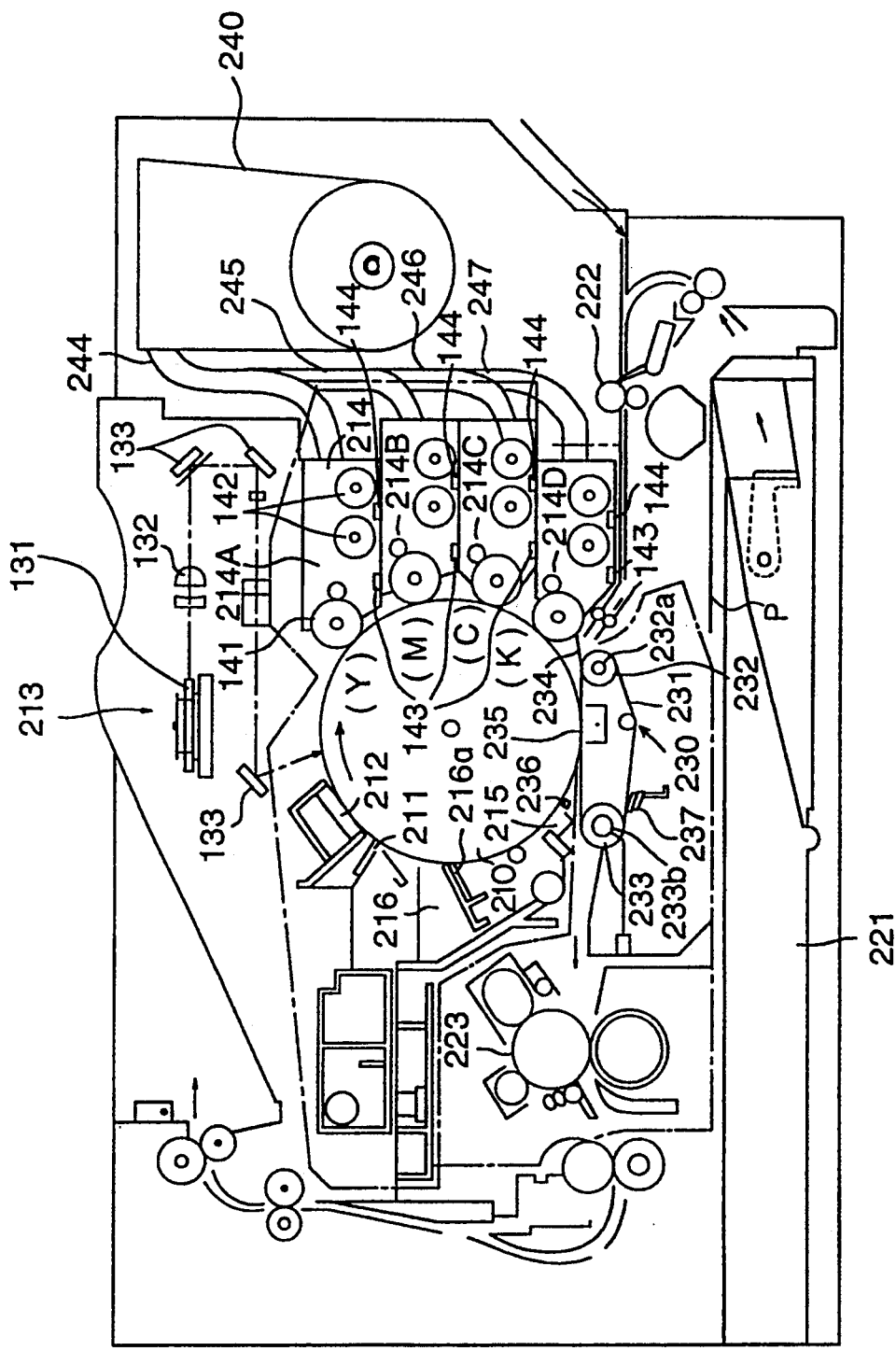
FIG. 12 is a view showing an image forming apparatus of an embodiment to accomplish the second object.

FIG. 12 is a sectional view showing an overall arrangement of the color laser printer relating that is an example of the present invention.

The arrangement and a series of operations will be briefly described as follows. The surface of a photoreceptor drum 210, which is an image carrier, is coated with an OPC photosensitive layer. The photoreceptor drum 210 is rotated in one direction, that is, the photoreceptor drum 210 is rotated clockwise in the case illustrated in the drawing. While the photoreceptor 210 is being rotated, it is neutralized by a PCL (neutralizer) 211 so that the electrical charge given in the previous printing process is removed. A circumferential surface of the photoreceptor drum 210 is uniformly charged by a charging unit 212 being ready for the next printing operation.

After the circumferential surface of the photoreceptor drum 210 has been uniformly charged, image exposure is conducted by an image exposure means 213 in accordance with an image signal. In the image exposure means 213, rotary scanning is conducted by the laser beams emitted from a laser beam source described later by the action of a polygonal mirror 131. Then, the laser beams pass through an $f\theta$ lens 132, and its optical path is bent by a reflection mirror 133. After that the laser beams are projected onto a circumferential surface of the photoreceptor drum 210 so that a latent image can be formed on the photoreceptor drum surface.

Around the photoreceptor drum 210, are provided developing units 214 in which developers containing toners of yellow (Y), magenta (M), cyan (C) and black (K), and magnetic carrier are respectively charged. Each of the developing units 214A to 214D includes a rotational developing sleeve 141 having a magnet, and a plurality of stirring screws 142 (stirring means) which are rotated synchronously with the developing sleeve 141. These developing sleeves and stirring screws are changed over in accordance with the color to be developed.

A developing operation is performed by the developing unit 214 in the following manner. First, development of the first color (for example, yellow) is conducted by a development sleeve 141 that is rotated while it is holding developer of the first color. A developer layer, the thickness of which is regulated to be a predetermined value by a layer forming rod, is formed on the development sleeve 141 and conveyed to a development region. Between the photoreceptor drum 210 and the development sleeve 141, is impressed a bias voltage in which AC bias $V_{AC}$ and DC bias $V_{DC}$ are superimposed. In this case, DC bias voltage $V_{DC}$ is determined so that the inequality of $V_H > V_{DC} > V_L$ can be satisfied, wherein a potential (ground potential) of an exposed portion of the photoreceptor drum 210 is $V_L$, and a surface potential of the charged photoreceptor layer on the photoreceptor drum 210 except for the exposed portion is $V_H$. When DC bias voltage $V_{DC}$ determined in the aforesaid manner is impressed, the toner is triggered to separate from the carrier. The separated toner does not deposit on a portion, the potential of which is $V_H$, wherein $V_H$ is higher than $V_{DC}$, but the separated toner deposits on an exposed portion, the potential of which is $V_L$, wherein $V_L$ is lower than $V_{DC}$. When the toner deposits in the aforesaid manner, the latent image is developed and visualized. In this case, each of the developing units 214A to 214D is provided with a concentration sensor 143 to detect the concentration of toner.

After the developing operation of the first color has been completed in the manner described above, the second color (for example, magenta M) image formation is started, that is, the photoreceptor drum 210 is uniformly charged, and a latent image is formed by the image exposure means 213 in accordance with image data of the second color. An image of the third color (cyan C) and that of the fourth color (black BK) are formed in the same manner. Accordingly, images of 4 colors are formed on the circumferential surface of the photoreceptor drum 210.

On the other hand, a recording paper P is fed from a paper feed cassette 221 by a paper feed mechanism 222. Then, the recording paper P is fed by a transfer belt unit 230 having a transfer belt 231, to a nip portion (transfer region) 235 formed between the photoreceptor drum 210 and a transfer belt 231. In the transfer region, the multiple color image formed on the circumferential surface of the photoreceptor drum 210 is entirely transferred onto the recording paper P. In this case, a high voltage is impressed upon a shaft 232a of a holding roller 232 provided on an upstream side of the transfer belt 231. A conductive brush 234 attached to the shaft 232a being opposed to the transfer belt 231, is grounded, and the conveyed recording paper P enters a space formed between the brush 234 and the transfer belt 231. Then an electrical charge is injected onto the recording paper P by the brush 234. While the recording paper P is attracted to the transfer belt 231 by the action of the injected electrical charge, the recording paper P enters the transfer region. The recording paper P that has been separated from the photoreceptor drum 210 is separated from the transfer belt 231 being neutralized while the shaft 233b of the holding roller 233 on the downstream side of the transfer belt 231 is used as an opposed electrode. In this case, the deposited toner on the transfer belt 231 is removed by a cleaning blade 237.

In this connection, while a multiple color image is being formed, the transfer belt 231 is separated from the surface of the photoreceptor drum 210 being rotated around a shaft 233b of the holding roller 233 on the downstream side.

After the recording paper P has been separated from the transfer belt unit 230, it is conveyed to a fixing unit 223 composed of two fixing rollers, wherein at least one of them is provided with a heater assembled inside the roller. When the recording paper P is heated and pressed by the fixing rollers, the deposited toner is fused and fixed on the recording paper P. After that, the recording paper is conveyed outside of the apparatus.

The residual toner on the circumferential surface of the photoreceptor drum 210 is neutralized by the neutralizer 215, and arrives at the cleaning unit 216. Then the residual toner is scarped off by a cleaning blade 216a so that it drops into the cleaning unit 216. Then the toner is conveyed by a screw conveyer and recovered by a recovery box. After the photoreceptor drum 210 has been cleaned by the cleaning unit 216, it is neutralized by the PCL 211, and uniformly charged by the charging unit 212. Then the photoreceptor drum 210 enters the next image formation cycle.

When the recording paper P is not separated from the transfer belt 231, it is wound around the photoreceptor drum 210 and enters the neutralizer 215. In this case, there is a possibility that the cleaning blade 216a and the electrode wire are damaged. In order to prevent the aforesaid problems, a JAM sensor 236 to detect the wound recording paper P is provided close to the neutralizer 215.

Figure 13:
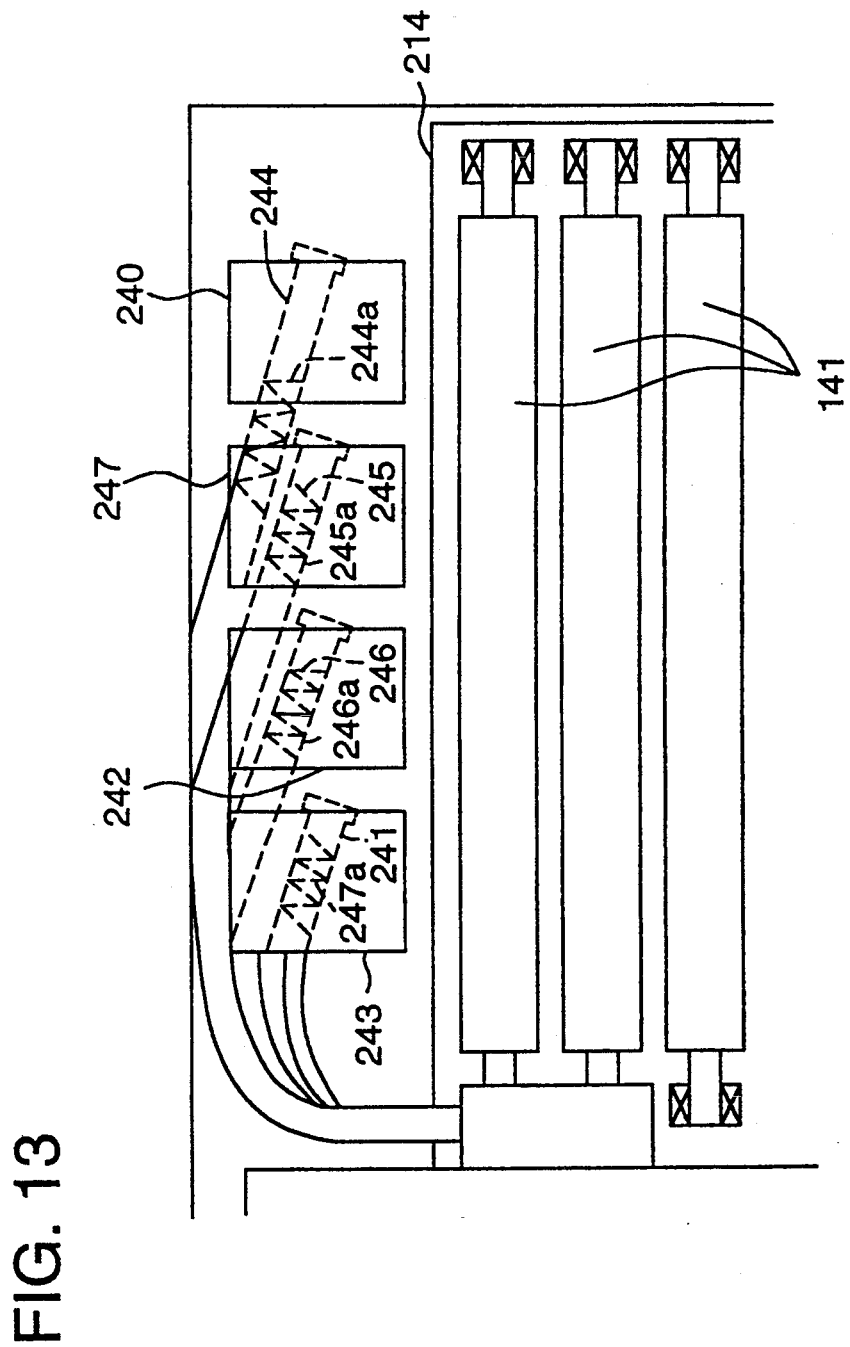
FIG. 13 is a view showing a toner replenishing mechanism of the image forming apparatus of the aforesaid embodiment.

In order to supply toner of each color to each of the developing units 214A to 214D, hoppers 240 to 243 are provided, and are also provided conveyance pipes 244 to 247 that convey toners in the hoppers 240 to 243, to the developing units 214A to 214D by the rotation of conveyance screws 244a to 247a installed in the hoppers 240 to 243 (shown in FIG. 13). In a normal printing mode, toner concentration of each developing unit is detected with the concentration sensor 143. In the case where the concentration of toner in a developing unit is lowered, toner is replenished to the developing unit 214 through a conveyance pipe when a toner conveyance screw in a hopper accommodating the corresponding toner is driven.

The example of the present invention is characterized in that: the fluidity sensor 144 to detect the fluidity of developer is attached to each of the developing units 214A to 214D.

As shown in FIG. 3, the fluidity sensor 144 is constructed in the following manner: The shear wave oscillator 1a to emit transverse ultrasonic waves is disposed so that developer particles can be deposited on a surface parallel to the oscillating direction of the oscillator 1a. When the fluidity of developer has been changed, in accordance with a change in the load with respect to the oscillation, the fluidity can be detected.

In this connection, numeral 1b is an electrode in FIG. 3.

In the above example, the fluidity sensor 144 having the shear wave oscillator 1a is attached to the developing unit 214. However, the fluidity sensor 144 may be attached to the hoppers 240 to 243, or the conveyance pipes 244 to 247, so that the toner fluidity can be detected. In the case of an image forming apparatus in which one-component developer composed of only toner is used being provided in a disposable cartridge, the fluidity sensor may be attached to the toner cartridge. A position where the fluidity sensor 144 is disposed is not limited to the specific example as far as the position is located between the toner storing portion and the developing sleeve.

It is also possible to detect an amount of residual developer in the following manner: The aforesaid fluidity detection is utilized, and it is judged whether or not the detected fluidity is at a level of non-contact with developer. In accordance with the judgment, the residual developer detection is performed.

In this case, when the fluidity of developer is lowered due to moisture, uneven or blurred toner images are formed, and the image quality is deteriorated. In order to solve the above problems, the detection result of the fluidity sensor 144 is used in the following manner so as to avoid the deterioration of image quality.

Figure 14:
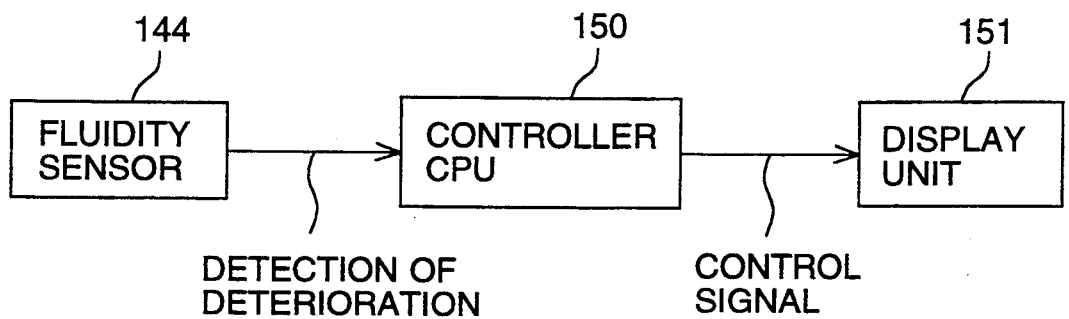
FIG. 14 is a block diagram showing am embodiment to display the result of detection of fluidity.

In the diagram shown in FIG. 14, the detection result of the fluidity sensor 144 is inputted into a CPU 150 for controlling a laser beam color printer of this example as one of the parameters.

In the construction shown in FIG. 14, a display unit (a liquid crystal display, CRT and LED) 151 controlled by the CPU 150 is attached to the printer. When the CPU 150 used for judging the fluidity judges that the fluidity of developer has been lowered to a predetermined value, the CPU for control use allows a displaying unit (displaying means) 151 to display the warning of deterioration in the fluidity. Accordingly, an operator is informed of the time at which the developer is replaced and also the necessity of replenishment of developer.

When the operator replaces or replenishes the developer in response to the warning, the problem of deterioration in the fluidity can be solved, so that the image quality can be maintained at a predetermined level.

Figure 15:
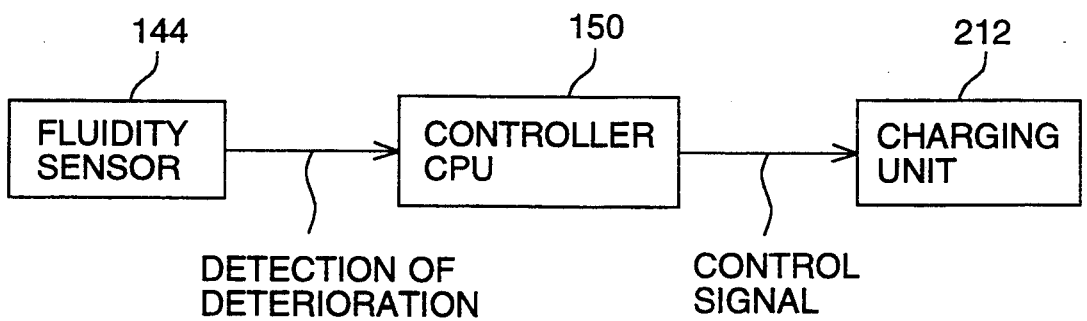
FIG. 15 is a block diagram showing an embodiment in which the charging potential is changed in accordance with the fluidity.

FIG. 15 shows a construction in which an electrically charging action conducted by the charger 212 on the photoreceptor drum 210 is controlled in accordance with the detection result of the fluidity sensor 144.

When the fluidity of developer is deteriorated, the deposition force among the developer particles is increased, so that the toner image can not be transferred in a good condition by the electrostatic attractive force generated between the toner particles and the photoreceptor drum 210. In order to take measures against the above problems, when the deterioration in fluidity is detected, the CPU 150 for control use increases the power to be given to the charger 212 for the purpose of increasing the aforesaid electrostatic attractive force so that the charging potential of the photoreceptor drum is raised. As a result, the toner particles can be positively transferred onto the surface of the photoreceptor drum 210.

Figure 16:
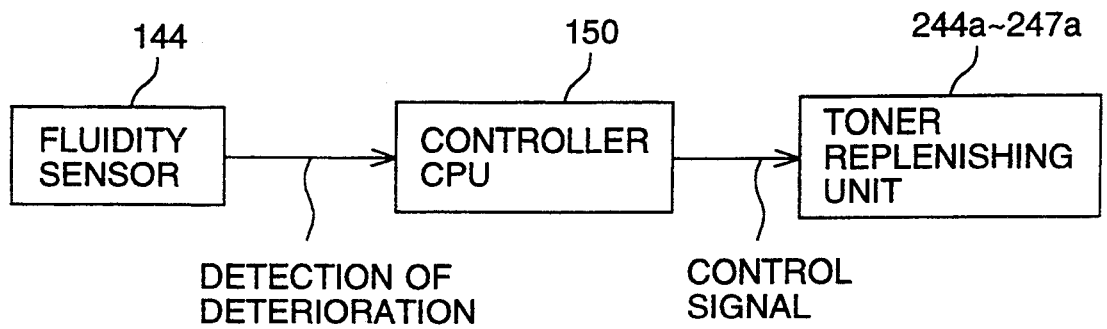
FIG. 16 is a block diagram showing an embodiment in which toner concentration is changed in accordance with the fluidity.

In the construction shown in FIG. 16, in the toner replenishment control in which a toner concentration sensor 143 provided in a developing unit 214 is used, the detection result provided by the fluidity sensor 144 is utilized.

In the present example, the toner concentration is controlled in the following manner: When the toner concentration is lowered in the developing unit 214, the toner of corresponding color is supplied to the developing unit 214 through one of the conveyance pipes 244 to 247 by rotating one of the conveyance screws (toner supply unit) 244a to 247a, so that the toner concentration is controlled to be a value appropriate for development. In the construction shown in FIG. 16, in accordance with the fluidity of developer detected by the fluidity sensor 144, the CPU 150 for control use changes the reference concentration used for toner concentration judgment. In the case where the fluidity of toner is deteriorated, the target concentration is raised in the toner concentration control.

In this connection, in the construction shown in FIG. 16, the CPU 150 for control use corresponds to a toner concentration control means.

When the toner concentration is increased to a value higher than a normal one as described above, the frequency of mis-transfer of toner particles can be reduced, so that the deterioration of image quality can be prevented.

Figure 17:
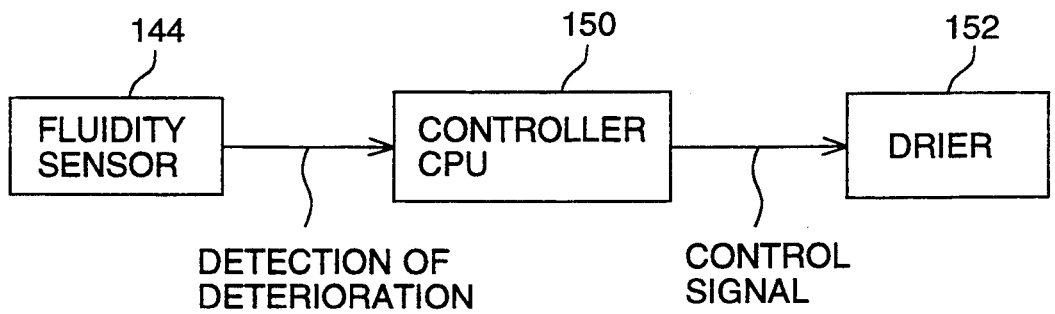
FIG. 17 is a block diagram showing an embodiment in which a drier is activated in accordance with the fluidity.
Figure 18:
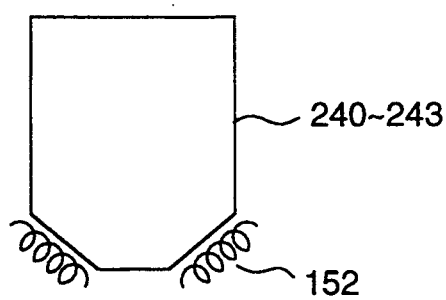
FIG. 18 is a view showing a specific embodiment of the drier.

In the construction shown in FIG. 17, a drier 152 (drying means) to dry developer is provided, and the CPU 150 for control use controls the drier 152 in accordance with the detection result provided by the fluidity sensor 144.

For example, the drier 152 is an electric heater attached to the hoppers 240 to 243. In the case where the deterioration in the fluidity of developer has been detected by the fluidity sensor 144, the CPU 150 for control use controls the drier 152 so that the drier can be operated and the developer is dried. In this way, the fluidity of developer can be recovered.

When the developer is moistened, the binding power of the developer particles is increased, so that the fluidity of developer is deteriorated. Consequently, it can be guessed that the deterioration in the fluidity has been caused by the moisture, and the drier 152 is operated to evaporate the moisture.

In this connection, an electric heater, blower and dehumidifier may be used for the drier 152.

Figure 19:
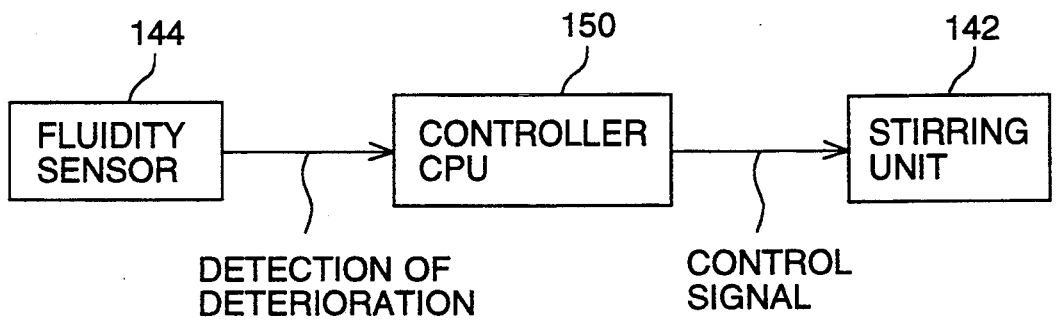
FIG. 19 is a block diagram showing an embodiment in which a stirring operation is controlled in accordance with the fluidity.

In the construction shown in FIG. 19, in accordance with the result of detection provided by the fluidity sensor 144, the driving force of a stirring screw 142 (a stirring unit) is controlled by the CPU 150 for control use which serves as a stirring control means.

According to the construction shown in FIG. 19, when the deterioration in fluidity is detected by the fluidity sensor 144, the rotational speed of the stirring screw 142 is increased, so that the stirring operation is conducted more intensely, and aggregated pieces of developer are smashed to recover the fluidity.

In the case of an apparatus for which a two component developer is used, the stirring screw 142 for stirring the two component developer is originally provided, so that the aggregated developer pieces can be smashed by the stirring screw 142. However, in the case of an apparatus for which one-component developer is used, a stirring screw for mixing is not provided, an exclusive stirring means for recovering fluidity may be provided.

Figure 20:
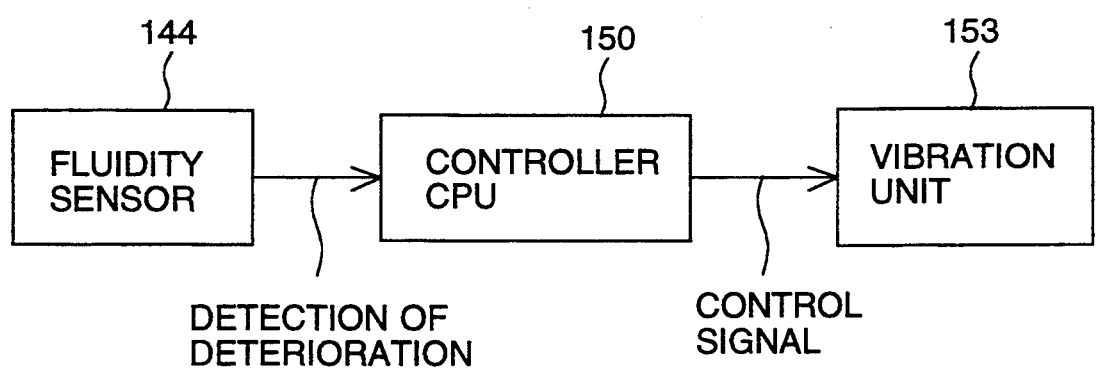
FIG. 20 is a block diagram showing an embodiment in which an oscillating unit is controlled in accordance with the fluidity.

In the construction shown in FIG. 20, the oscillation devices (oscillators) 153 to solve the problem of aggregation of developer are provided in the developing unit 14, hoppers 240 to 243, and conveyance pipes 244 to 247 (or disposable toner cartridges), and the operation of the oscillation device 153 is controlled by the CPU 150 which is an oscillation control means to which a detection signal of the fluidity sensor 144 is inputted.

When the deterioration in the fluidity of developer is detected, the oscillation devices 153 are activated so as to smash the aggregated pieces of developer, and the fluidity can be recovered.

In this connection, the constructions shown in FIGS. 14, 17, 19 and 20 may be combined so as to concurrently carry out a plurality of operations. Also, a plurality of fluidity sensors 144 may be disposed in the path for supplying developer, and different counter measures may be taken in accordance with a position where the deterioration in fluidity has been detected.

In this example, a color printer is taken for an example, however, the present invention may be applied to a copier to which an optical image of documents is directly guided onto a photoreceptor drum 210, and a monochromatic printer.

As explained above, according to the present invention, in an image forming apparatus by which a toner image is developed, the fluidity of developer used for development can be detected in quick response under the condition that the developer is put in a container. Further, in accordance with the result of detection of developer fluidity, various measures are taken such as giving a warning of deterioration in the fluidity, increasing the charging potential, increasing the toner concentration, conducting a drying processing, increasing the driving force, and oscillating the developer. Due to the foregoing, the deterioration in image quality caused by lowered fluidity can be prevented.

Next, an example to accomplish the third object will be explained as follows.

In this example, the residual toner amount detection sensors 144 are provided on the wall surfaces of the hoppers 240 to 243.

Figure 21:
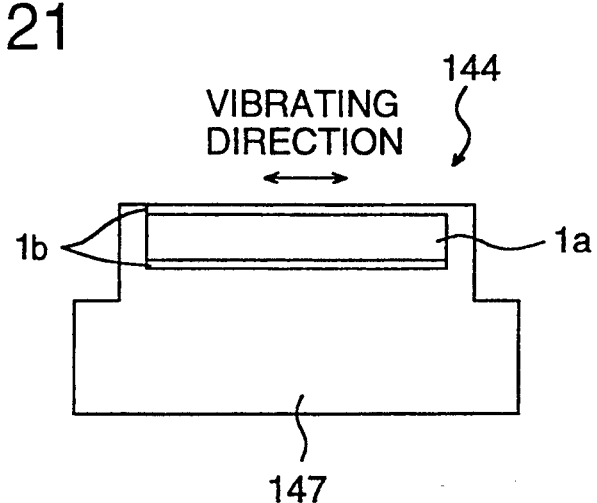
FIG. 21 is a view showing a residual toner amount detection sensor used for an embodiment to accomplish the third object.

As shown in FIG. 21, the residual toner amount detection sensor 144 includes: a sensor element composed of a shear wave oscillator (piezoelectric oscillator) 1a to emit transverse ultrasonic waves, and a pair of electrodes 1b provided on both sides of the piezoelectric oscillator; and a casing 147 to which the sensor element is attached. The residual toner amount detection sensor 144 is attached onto the wall surface of each of hoppers 240 to 243 at a position of a predetermined height in such a manner that one side of the detection sensor 144 parallel with the oscillating direction is opposed to each of the hoppers 240 to 243.

Figure 22:
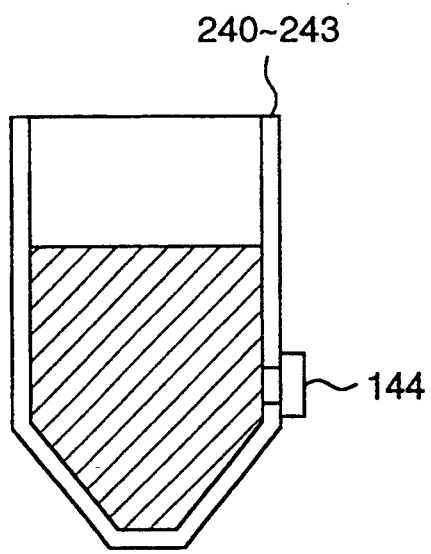
FIGS. 22(A) and 22(B) are views showing a positional relation of the residual toner amount detection sensor in a hopper.
Figure 22:
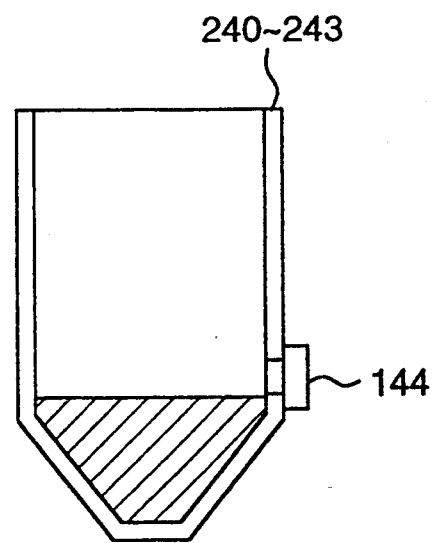

Due to the foregoing, when a level of the residual toner amount is higher than that of the detection sensor 144 as illustrated in FIG. 22(A), the toner comes into contact with the surface of the detection sensor 144 that is parallel with the oscillating direction of the shear wave oscillator 1a. When the level of the residual toner amount is lower than that of the detection sensor 144 as illustrated in FIG. 22(B), the surface of the shear wave oscillator 1a comes into contact with air.

In the above construction of the piezoelectric element, the electrical impedance is affected by a medium contacting with the surface of the oscillator, the surface being parallel with the oscillating direction. In the case where the oscillating direction is longitudinal, that is, in the case where the oscillating direction is perpendicular to the boundary surface coming into contact with the medium, the electrical impedance is changed by the pressure of the medium. However, in this example, the oscillating direction is parallel with the boundary surface. In this case, the electrical impedance is changed in accordance with the viscosity of the medium coming into contact with the boundary surface. In this case, the viscous resistance of toner is much higher than that of air. Therefore, the electrical impedance is greatly changed when the contacting medium is changed from toner to air as illustrated in FIGS. 22(A) and 22(B).

When the shear wave oscillator 1a is combined with an oscillating circuit, it oscillates at a resonance frequency. In the case where a medium having a mechanical impedance adheres onto a surface of the oscillator, that is, an electrode surface of the oscillator under the aforesaid resonance condition, the electrical impedance of the oscillator is increased. As a result of the foregoing, the resonance frequency of the oscillator is lowered and resonance sharpness Q is decreased. Consequently, when these phenomena are taken out by the detection circuit, it can be detected whether or not toner comes into contact with the electrode surface of the shear wave oscillator 1a, in other words, it can be detected whether or not the residual toner amount is a predetermined value.

Figure 23:
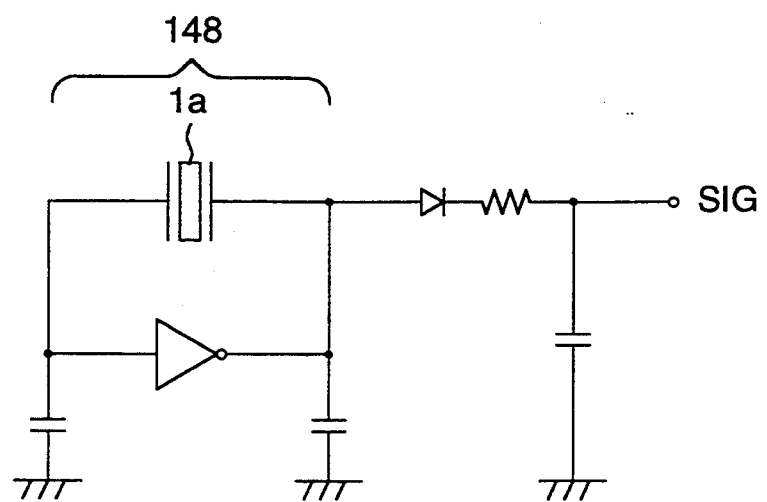
FIG. 23 is a view showing a detection circuit for the residual toner amount detection sensor.

FIG. 23 is a circuit diagram showing an example of the aforesaid oscillation and detection circuit.

As shown in FIG. 23, a self-excited oscillating circuit 148 is composed of the shear wave oscillator 1a, and ,whether or not toner exists, that is, a residual toner amount can be detected in accordance with a level of the output signal SIG sent from the self-excited oscillating circuit 148.

Figure 24:
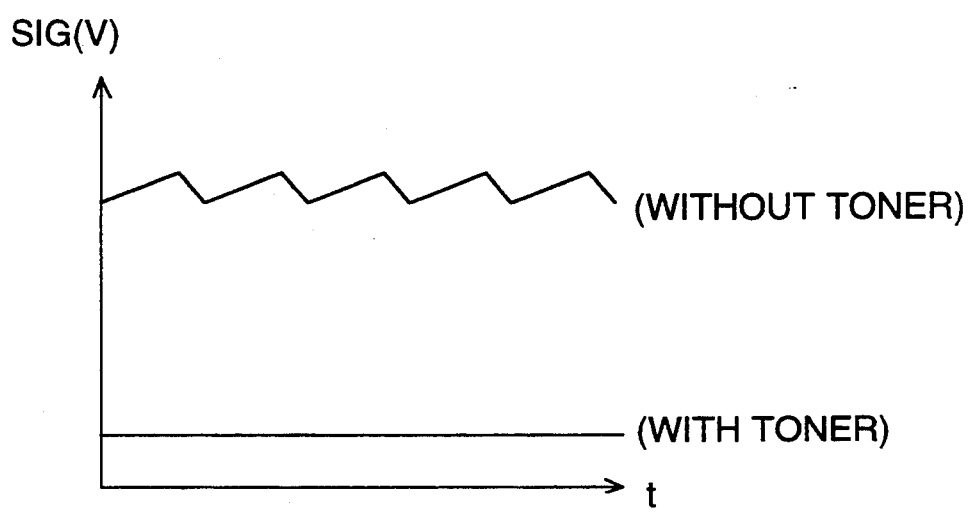
FIG. 24 is a view showing a difference of the detection signal level in accordance with a residual toner amount.

When a level of toner is lowered and the level becomes lower than that of the residual toner amount detection sensor 144 as shown in FIG. 22(b) so that air comes into contact with the shear wave oscillator 1a, the viscous resistance (impedance) of air is lower than that of toner. Therefore, a high output signal SIG can be provided as shown in FIG. 24. When a level of the residual toner is higher than that of the residual toner amount detection sensor 144, the level of the output signal SIG is lowered as shown in FIG. 24 since the viscous resistance of toner is much higher that of air.

Accordingly, when the level of the output signal SIG is discriminated by a predetermined threshold value, it can be judged whether or not toner exists. When it has been detected by the residual toner amount detection sensor 144 that the residual toner amount is smaller than a predetermined value, a warning lamp provided on the printer is lit so as to warn an operator of a toner shortage.

In this case, even when the fluidity of toner is changed due to the moisture, or even when the toner type is changed, a level of toner can be clearly discriminated from that in a condition in which the sensor surface is contacted with air. Therefore, even when the toner type is changed or toner is aggregated by the influence of moisture, the residual toner amount can be accurately detected without being affected by the moisture or the change in toner type.

For this reason, it is not necessary to adjust the detection sensor for each type of toner, and even when toner is aggregated, the detection accuracy can be maintained high and the residual toner amount can be stably carried out.

In this case, instead of the detection method shown in FIG. 23, the following construction may be employed: A ratio of the amplitude of an AC signal inputted into the shear wave oscillator 1a, to the amplitude of a signal that has passed through the shear wave oscillator 1a, is measured by changing the frequency, and a change in the impedance is detected in the form of a change in a ratio of the input amplitude to the output amplitude (=input amplitude/output amplitude) .

Further, the following construction may be employed: A detection circuit to detect the resonance frequency of the shear wave oscillator 1a is provided. When a change in the resonance frequency caused by the existence of toner is detected, a residual toner amount is detected. Also, the resonance sharpness Q is measured in the case of resonance, and a residual toner amount is detected by a change in the resonance sharpness Q caused by the existence of toner.

In this connection, under a condition that toner comes into contact with the shear wave oscillator 1a, a change in the viscous resistance of toner affects the impedance. Therefore, it is possible to detect the viscous resistance of toner (fluidity) by the aforesaid residual toner amount detection sensor 144.

In this example, a color printer is taken for an example, however, the present invention may be applied to a copier to which an optical image of documents is directly guided onto a photoreceptor drum 210, and a monochromatic printer.

As described above, according to the present invention, a residual toner amount is detected in the following manner: When a medium is changed which comes into contact with a surface parallel with the oscillating direction of a piezoelectric element to generate a shear wave oscillation, the electrical impedance of the piezoelectric element is changed. Utilizing the aforesaid phenomenon, a residual toner amount is detected from a large difference between the viscous resistance of toner and that of air. Consequently, the residual toner amount can be stably and accurately detected without being affected by the type of toner.

What is claimed is:

1. A method for detecting a fluidity of powder, comprising said steps of:
   (a) making said powder come into contact with a surface of a piezoelectric element being parallel with an oscillating direction of said piezoelectric element that generates transverse wave oscillations;
   (b) detecting electrical characteristics of said piezoelectric element under a condition of resonance; and
   (c) detecting said fluidity of said powder in accordance with a change in said electrical characteristics with respect to a reference value.

2. The method for detecting a fluidity of powder of claim 1, wherein said electrical characteristics of said piezoelectric element comprises an impedance.

3. The method for detecting a fluidity of powder of claim 1, wherein said electrical characteristics of said piezoelectric element is a resonance frequency.

4. The method for detecting a fluidity of powder of claim 1, wherein said electrical characteristics of said piezoelectric element is a resonance sharpness.

5. A fluidity detection sensor for detecting a fluidity of powder, comprising:
   a piezoelectric element for generating transverse wave oscillations;
   said piezoelectric element being arranged so that said powder is contacted with a surface of said piezoelectric element that is in parallel with an oscillating direction of said piezoelectric element;
   a first detector for detecting both an electrical characteristic and a resonant frequency of said piezoelectric element under a condition of resonance; and
   a second detector for detecting the fluidity of said powder in accordance with a change in said electrical characteristic at the resonant frequency of said piezoelectric element under said condition of resonance and with respect to a reference value.

6. The sensor for detecting a fluidity of powder of claim 5, wherein said electrical characteristic of said piezoelectric element comprises an impedance.

7. The sensor for detecting a fluidity of powder of claim 6, further comprising:
   a sensing device for obtaining said reference value, said sensing device including:
      another piezoelectric element for generating transverse wave oscillations;

said another piezoelectric element being arranged so that said powder is noncontacted with a surface thereof that is in parallel with an oscillating direction of said another piezoelectric element; and a third detector for detecting an impedance of said another piezoelectric element at said resonant frequency of said first detector and with respect to said reference value;

wherein said second detector comprises a circuit for detecting a ratio between an impedance of said piezoelectric element obtained at the resonant frequency of said first detector and said impedance of said another piezoelectric element detected by said third detector.

8. The sensor for detecting a fluidity of powder of claim 5, wherein said electrical characteristic of said piezoelectric element is a resonance frequency.

9. The sensor for detecting a fluidity of powder of claim 8, further comprising:

a sensing device for obtaining said reference value, said sensing device including:

another piezoelectric element for generating transverse wave oscillations;

said another piezoelectric element being arranged so that said powder is noncontacted with a surface thereof that is in parallel with an oscillating direction of said another piezoelectric element; and a third detector for detecting a resonant frequency of said another piezoelectric element at said resonant frequency of said first detector and with respect to said reference value;

wherein said second detector comprises a circuit for detecting a difference in frequency between said resonant frequency of said first detector and said resonant frequency of said another piezoelectric element detected by said third detector.

10. The sensor for detecting a fluidity of powder of claim 5, wherein said electrical characteristic of said piezoelectric element is a resonance sharpness.

11. The image forming apparatus, comprising:

a photoreceptor;

a developing unit with developer for developing latent images on said photoreceptor;

a toner container for supplying toner to said developing unit; and a sensor device provided in said toner container to be in contact with the developer for detecting a condition of said developer, said sensor device including:

a piezoelectric element provided to be in contact with the developer; a surface of said piezoelectric element contacting said developer being in parallel with an oscillating direction of said piezoelectric element for generating transverse wave oscillations when said condition of said developer is above a reference value; and a detector for detecting said transverse wave oscillations of said piezoelectric element and for detecting an electrical characteristic of said piezoelectric element at a resonant frequency of said piezoelectric element.

12. The image forming apparatus of claim 11, wherein said condition of said developer is an amount of residual toner.

13. The image forming apparatus of claim 12, further comprising:

another detector for detecting a residual amount of said developer in accordance with a change in said electrical characteristic of said piezoelectric element with respect to said reference value and wherein said another detector outputs a detection signal.

14. The image forming apparatus of claim 11, wherein said condition of said developer is a fluidity of said developer.

15. The image forming apparatus of claim 14, further comprising:

another detector for detecting the fluidity of said developer in accordance with a change in said electrical characteristic with respect to a reference value and for outputting a detection signal.

16. The image forming apparatus of claim 15, wherein said electrical characteristic of said piezoelectric element is an impedance.

17. The image forming apparatus of claim 15, wherein said electrical characteristic of said piezoelectric element is a resonance frequency.

18. The image forming apparatus of claim 15, wherein said electrical characteristic of said piezoelectric element is a resonance sharpness.

19. The image forming apparatus of claim 15, further comprising:

a display for displaying a deterioration of the fluidity in accordance with said detection signal.

20. The image forming apparatus of claim 15, further comprising:

a controller for controlling a charging potential of said photoreceptor in accordance with said detection signal.

21. The image forming apparatus of claim 20, further comprising:

a toner concentration controller for controlling a toner concentration in said developing unit in accordance with said detection signal.

22. The image forming apparatus of claim 15, further comprising:

a dryer for drying said developer; and a dryer controller for activating said dryer in accordance with said detection signal.

23. The image forming apparatus of claim 15, wherein said developer comprises a toner and a carrier.

24. The image forming apparatus of claim 23, further comprising:

a stirrer for stirring said toner, and a stirrer controller for activating said stirrer in accordance with said detection signal.

25. The image forming apparatus of claim 24, further comprising:

an oscillator for oscillating said developer, and an oscillator controller for activating said oscillator in accordance with said detection signal.

26. The image forming apparatus of claim 15, further comprising:

a hopper for containing toner, a conveyance pipe for conveying said toner from said hopper to said developing unit.

27. The image forming apparatus of claim 26, wherein said sensor device is provided in said hopper.

28. The image forming apparatus of claim 26, wherein:

said sensor device is provided in said conveyance pipe.

29. The image forming apparatus of claim 26, further comprising:

a toner cartridge for containing toner, and wherein said sensor device is provided in said toner cartridge.

* * * * *